United States Patent
Spengler et al.

(12) 
(10) Patent No.: US 6,669,879 B1
(45) Date of Patent: Dec. 30, 2003

(54) METHOD FOR PRODUCING SOLID DOSING FORMS

(75) Inventors: Reinhard Spengler, Maxdorf (DE); Jörg Rosenberg, Ellerstadt (DE)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/763,662

(22) PCT Filed: Aug. 27, 1999

(86) PCT No.: PCT/EP99/06314

§ 371 (c)(1), (2), (4) Date: Feb. 26, 2001

(87) PCT Pub. No.: WO00/12068

PCT Pub. Date: Mar. 9, 2000

(30) Foreign Application Priority Data

Aug. 28, 1998 (DE) .......................................... 198 39 276

(51) Int. Cl.[7] .................................................. B29B 9/10
(52) U.S. Cl. ........................ 264/112; 264/141; 264/300
(58) Field of Search ................................ 264/112, 141, 264/299, 300, 310; 425/363

(56) References Cited

U.S. PATENT DOCUMENTS

| 4,880,585 A | 11/1989 | Klimesch et al. ............ 264/141 |
| 5,897,910 A | 4/1999 | Rosenberg et al. ......... 427/2.14 |
| 6,001,391 A | 12/1999 | Zeidler et al. ............... 424/467 |

FOREIGN PATENT DOCUMENTS

| AU | 702198 | 9/1996 |
| EP | 0 590 963 | 4/1994 |
| WO | WO 93/07859 | 4/1993 |

*Primary Examiner*—Mary Lynn Theisen
(74) *Attorney, Agent, or Firm*—Keil & Weinkauf

(57) ABSTRACT

A process for producing solid dosage forms by forming a plastic mixture of at least one polymeric binder, at least one active ingredient and, where appropriate, conventional additives, and shaping the plastic mixture to the solid dosage forms using a mold, wherein an agent which modifies the surface properties is applied in finely divided form to the surface of the plastic, mixture during the shaping is described. The agent which modifies the surface properties is preferably a surfactant, a lipophilic compound, an antioxidant, a coloring agent or an agent with antistatic effect and/or lubricant effect.

9 Claims, No Drawings

METHOD FOR PRODUCING SOLID DOSING FORMS

The present invention relates to a process for producing solid dosage forms by forming a plastic mixture of at least one polymeric binder, at least one active ingredient and, where appropriate, conventional additives, and shaping the plastic mixture to the solid dosage forms using a mold.

The production of solid dosage forms by extrusion and subsequent calendering of an active ingredient-containing melt is disclosed, for example in DE-A-17 66 546 and U.S. Pat. No. 4,880,585. This process is based on the embedding of an active ingedient in a melt of a carrier, for example fatty substances or water-soluble, thermoplastic polymers. The melt is produced by melting the mixture of active ingredient, polymer and, where appropriate, other ancillary substances, for example in an extruder, and shaping as melt in a subsequent shaping calender to tablets, which harden by cooling.

Solid dosage forms ordinarily contain not only the carrier substance but also one or more ancillary substances. On the hand, these ancillary substances are often indispensable in order to control the release of the active ingredient, to prevent decomposition of the active ingredient due to light and/or oxidation, to mask an unpleasant taste of the active ingredient, to make the dosage forms colored for easier identification etc. On the other hand, ancillary substances are usually necessary in order to ensure satisfactory industrial processability of the dosage forms during production, during subsequent processing steps etc.

The required ancillary substances are usually incorporated into the tablet composition, i.e. in the finished dosage forms, they are uniformly distributed in the volume of the dosage forms. However, most of the ancillary substances employed display their effect only on the surface of the dosage forms. This means that only the portion of the ancillary substances located in the outermost surface layer and a few micrometers below that contributes to the required effect. In order to have a sufficient concentration at the surface, it is therefore necessary for these ancillary substances to be incorporated in relatively high concentration into the tablet composition. Most of the ancillary substance in the tablet volume remains without effect, which makes the production of the tablets unnecessarily costly. There may also be unwanted interactions of the ancillary substance with the active ingredient or with the substances forming the matrix.

In addition, the freedom of formulating the tablet composition is restricted because it is possible to use only active ingredients and ancillary substances which are compatible with one another.

On the other hand, it is known to coat tablets in the last step of manufacture with a thin layer of, for example, water-soluble polymers. Film-coated tablets are produced in this way. If a coating was required over the tablets produced by melt calendering, it was necessary to apply this coating in a separate step after cooling of the tablets. This took place in a conventional way, for example by spraying on in rotating drums, by dipcoating or in a fluidized bed etc. The conventional processes for applying coating layers all require a comparatively large energy input because the solvents used in the spray solutions must be removed again rapidly after spraying onto the tablets. In addition, a coating process usually takes several hours because the spraying rate cannot be set as high as desired.

WO 96/19963 describes a process for producing coated tablets by melt calendering, in which the active ingredient-containing melt is introduced between two sheets of the coating material into the calender molding rolls. This process is, however, suitable only for ancillary substances which can easily be produced in the form of a sheet.

DE-A-44 46 467 describes a process for producing lenticular tablets by melt calendering. It is pointed out in this publication that molding rolls provided with a release agent can be used. An example of a suitable release agent is a silicone paint. This suggests that the molding rolls are lined only once with the release agent and there is no transfer of the release agent from the molding rolls to the mixture to be tableted.

It is an object of the present invention to provide a process for producing solid dosage forms by melt extrusion, in which a modification of the surface properties of the solid dosage forms is possible in a simple and cost- and material-saving manner.

We have found that this object is achieved by applying an agent which modifies the surface properties in finely divided form to the surface of the plastic mixture during the shaping. The outer surface of the plastic mixture which is created by the shaping to solid dosage forms is in this way provided with an agent which modifies the surface properties.

The present invention therefore relates to a process for producing solid dosage forms by forming a plastic mixture of at least one polymeric binder, at least one active ingredient and, where appropriate, conventional additives, and shaping the plastic mixture to the solid dosage forms using a mold, wherein an agent which modifies the surface properties is applied in finely divided form to the surface of the plastic mixture during the shaping. The process according to the invention is preferably carried out continuously. It is essential for the process according to the invention that a continuous supply of agent which modifies the surface properties is ensured. It is also important that the agent which modifies the surface properties is applied at a time at which the plastic mixture has not yet completely solidified.

The term "shaping" may comprise the steps of preforming and definitive shaping. "Preforming" means every procedure in which the ratio of the surface area to the volume of the plastic mixture already substantially approximates to that of the finished dosage form. The preformed plastic mixture is preferably exposed to negligible shear forces during the definitive shaping, so that surface elements are not mixed into the interior.

Preforming is regarded as being, for example, the extrusion of the plastic mixture to give a ribbon or a sheet. It is thus possible within the scope of the present invention to apply the agent which modifies the surface properties to the surface of the preformed plastic mixture, e.g. of the ribbon or sheet, which is subsequently subjected to the definitive shaping.

The process according to the invention makes a considerable saving of ancillary substances possible without losses of efficacy because the dosage forms obtained according to the invention contain the ancillary substances predominantly or exclusively on their surface, while the concentration of ancillary substances over the volume of the dosage forms can be reduced, or the composition to be tableted can be kept free of ancillary substances.

The agent which modifies the surface properties is applied in finely divided form. This means that the agent is in powdered or liquid form and not in compact form, e.g. as sheet. The agent which modifies the surface properties can be applied in the form of a powder, a solution, a suspension, emulsion or dispersion. Where carrier liquids are required to produce a solution, suspension, emulsion or dispersion, these can be chosen to be volatile or else involatile.

Agents which modify the surface properties mean for the purpose of the invention all pharmaceutically suitable ancillary substances which alter the physical and/or chemical properties of the dosage forms which are caused wholly or partly by surface effects, e.g. color, pourability, separation characteristics, surface slip, sievability, permeability for vapors and/or gases, transparency, lipophilicity/hydrophilicity, redox potential, surface tension etc. They comprise ancillary substances normally incorporated into the tablet composition, and those whose use is made possible by the present invention for the first time.

Depending on the nature of the agent used to modify the surface properties, it is embedded or partly dissolved in the surface of the plastic mixture. In each case, the aim is permanent attachment of the agent which modifies the surface properties to the resulting dosage forms.

In a preferred embodiment of the invention, the agent which modifies the surface properties is a surfactant, preferably with an HLB of more than 10. Surfactants are able to increase the wettability of the dosage forms and thus improve the dissolving properties. In addition, surfactants may improve the release properties of the dosage forms. Suitable surfactants which may be mentioned are: fatty acid monoesters of polyhydroxyethylene sorbitan such as polyethylene glycol 20 sorbitan monolaurate (HLB 16.7), polyethylene glycol 20 sorbitan monostearate (HLB 14.9), polyethylene glycol 20 sorbitan monooleate (HLB 15.0), polyhydroxyethylene fatty alcohol ethers or fatty acid esters, such as polyhydroxyethylene cetylstearyl ether (Cremophor®O, HLB 16.1), polyhydroxyethylene 23 lauryl ether (HLB 16.9), polyhydroxyethylene 8 stearate (HLB 11.1), polyhydroxyethylene 40 stearate (HLB 16.8), polyhydroxyethylene 100 stearate (HLB 18.8), ethylene oxide propylene oxide block copolymers (Pluronic®), ethoxylated triglycerides, e.g. polyethoxylated castor oil 40 (Cremophor®EL; HLB 12–14), polyethoxylated hydrogenated castor oil 40 (Cremophor®RH; HLB 14–16).

In another preferred embodiment of the invention, the agent which modifies the surface properties is a lipophilic compound which is preferably selected from glycerides, waxes, fatty acids, fatty alcohols, paraffins, silicones and phosphatides. The use of a lipophilic compound for the purpose of the present invention allows the surface of the dosage forms to be made lipophilic. It is possible in this way, for example, to delay the release of the active ingredient and thus the onset of action of a drug product. It is additionally possible to reduce the adhesion of dosage forms stored as loose material. The penetration of water or water vapor or other constituents of the air into the dosage form can be reduced or suppressed, which has advantageous effects on the storage stability of the dosage forms. Examples of lipophilic compounds which are suitable for the purpose of the invention are, inter alia, hydrocarbons such as liquid and solid paraffin, petrolatum; fatty alcohols such as cetyl alcohol, stearyl alcohol, cetostearyl alcohol (Lanette®O), 2-octyldodecanol (Eutanol®G); fatty acids such as stearic acid; salts of fatty acids such as magnesium stearate, calcium stearate; glycerides such as arachis oil, olive oil, sesame oil, hydrogenated arachis oil, hydrogenated cottonseed oil, hydrogenated castor oil, semisynthetic and synthetic glycerides; waxes such as beeswax, carnauba wax, cetyl palmitate, wool wax (Lanolin®), isopropyl myristate, isopropyl stearate, Cetiol®V, ethyl oleate; phosphatides such as egg lecithin or soybean lecithin.

In another preferred embodiment of the invention, the agent which modifies the surface properties is an antioxidant which is preferably selected from ascorbic acid, ascorbyl palmitate, butylated hydroxytoluene, butylated hydroxyanisole, propyl gallate and tocopherols. Wax-like antioxidants, in particular with a melting point of less than 100° C., are preferred. The use of an antioxidant prevents oxidation-sensitive ingredients of the dosage forms being oxidized by entry of atmospheric oxygen during storage.

In another preferred embodiment of the invention, the agent which modifies the surface properties is a coloring agent, e.g. a soluble dye or else an inorganic or organic pigment. Suitable coloring agents which may be mentioned are iron oxides, talc, calcium carbonate, titanium dioxide, for example organic dyes laked with alumina, such as erythrosine, orange yellow S, tartrazine, indigotine, Ponceau 4 R, quinoline yellow, patent blue V; azo dyes etc. It has emerged that the use of insoluble colored pigments such as iron oxides is associated with an improvement in the release properties.

In another preferred embodiment of the invention, the agent which modifies the surface properties is an agent with antistatic effect and/or lubricant effect. Antistatic agents improve the pourability, the separation characteristics, the surface slip and the sievability of the dosage forms. Suitable antistatic agents which may be mentioned are, inter alia, glycol, glycerol, Aerosil, polyethylene glycol esters, polyethylene glycol, dicalcium phosphate and lactose. Lubricants are used to improve the release of the dosage forms from the mold. Suitable lubricants which may be mentioned are, inter alia, magnesium stearate, calcium behenate, sodium stearylfumarate, polyethylene glycols, phosphatidylcholine derivatives, stearic acid, talc, Aerosil, calcium stearate, glycerol esters, hydrogenated cottonseed oil, hydrogenated castor oil and rice starch.

It is self-evident that an agent which modifies the surface properties may be subsumed simultaneously by more than one of the abovementioned preferred embodiments. On the other hand, it is possible for agents which modify surface properties from two or more of the abovementioned embodiments to be combined and applied simultaneously or successively.

It is generally preferred for the agent which modifies the surface properties or the mixture of agents which modify the surface properties to comprise about 0.01 to 1.0% by weight, preferably about 0.01 to 0.5% by weight, in particular about 0.01 to about 0.3% by weight, based on the total weight of the resulting solid dosage form.

Dosage forms mean in the present case all forms suitable for use as drug products, crop treatment products, animal food products and human food products and for delivering fragrances and perfume oils. These include, for example, tablets of every shape, pellets, granules, but also larger forms such as cubes, blocks (bricks) or cylindrical forms, which can be used in particular as animal food or human food products.

The plastic mixture generally comprises:
a) 0.1 to 90% by weight, in particular 0.1 to 60% by weight (based on the total weight of the dosage form) of an active ingredient,
b) 10 to 99.9% by weight, in particular 40 to 99.9% by weight, of a polymeric binder, and
c) where appropriate additives.

The binder should preferably be soluble or swellable in a physiological environment. Examples of suitable binders are polyvinylpyrrolidone (PVP), copolymers of N-vinylpyrrolidone (NVP) and vinyl esters, in particular vinyl acetate, copolymers of vinyl acetate and crotonic acid, partially hydrolyzed polyvinyl acetate, polyvinyl alcohol, poly(hydroxyalkyl acrylates), poly(hydroxyalkyl methacrylates), polyacrylates and polymethacrylates (Eudragit types), copolymers of methyl methacrylate and acrylic acid, cellulose esters, cellulose ethers, in particular methylcellulose and ethylcellulose, hydroxyalkyl celluloses, in particular hydroxypropylcellulose, hydroxyalkylalkylcelluloses, in particular hydroxypropylethylcellulose, cellulose phthalates, in particular cellulose acetate phthalate and hydroxypropylmethylcellulose phthalate, starch, starch derivatives, e.g. maltodextrins, sugar alcohols, such as mannitol or palatinose and mannans, in particular galactomannans. The K values (method of H. Fikentscher, Cellulose-Chemie 13, 1932, 58–64 and 71–74) of the polymers are in the range from 10 to 100, preferably 12 to 70, in particular 12 to 35, and for PVP preferably 12 to 35, in particular 12 to 17.

The polymeric binder must soften or melt in the complete mixture of all the components in the range from 50 to 180, preferably 60 to 130° C., so that the composition can be extruded. The glass transition temperature of the mixture must therefore be below 180° C., preferably below 130° C. If necessary, it is reduced by conventional pharmacologically acceptable, plasticizing ancillary substances such as long-chain alcohols, ethylene glycol, propylene glycol, glycerol, trimethylolpropane, triethylene glycol, sugar alcohols, e.g. butanediols, pentanols, and pentaerythritol or hexanols, polyethylene glycols, polypropylene glycols, polyethylene/propylene glycols, silicones, aromatic carboxylic esters (e.g. dialkyl phthalates, trimellitic esters, benzoic esters, terephthalic esters) or aliphatic dicarboxylic esters (e.g. dialkyl adipates, sebacic esters, azelaic esters, citric and tartaric esters), fatty acid esters such as glycerol mono-, glycerol di- or glycerol triacetate or sodium diethyl sulfosuccinate. The concentration of plasticizer is generally 0.5 to 15% by weight, preferably 0.5 to 5% by weight, based on the total weight of the composition. The mixture preferably comprises no plasticizer. Active pharmaceutical ingredients for the purpose of the invention mean all substances with a pharmaceutical effect and minimal side effects as long as they do not decompose under the processing conditions. The amount of active ingredient per dose unit and the concentration may vary within wide limits depending on the activity and release rate. The only condition is that they suffice to achieve the desired effect. Thus, the active ingredient concentration may be in the range from 0.1 to 95, preferably from 20 to 80, in particular 30 to 70, % by weight. It is also possible to employ combinations of active ingredients, e.g. ibuprofen/caffeine. Active ingredients for the purpose of the invention are also vitamins and minerals, and crop treatment agents and insecticides. The vitamins include the vitamins of the A group, the B group, meaning not only $B_1$, $B_2$, $B_6$ and $B_{12}$ and nicotinic acid and nicotinamide but also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides.

Active ingredients mean for the purpose of the invention all substances with a physiological action as long as they do not decompose under the processing conditions. They are, in particular, active pharmaceutical ingredients (for humans and animals), active ingredients for crop treatment, insecticides, active ingredients for animal food and human food products, fragrances and perfume oils. The amount of active ingredient per dose unit and the concentration may vary within wide limits depending on the activity and release rate. The only condition is that they suffice to achieve the desired effect. Thus, the active ingredient concentration may be in the range from 0.1 to 95, preferably from 20 to 80, in particular 30 to 70, % by weight. It is also possible to employ combinations of active ingredients. Active ingredients for the purpose of the invention are also vitamins and minerals. The vitamins include the vitamins of the A group, the B group, meaning not only $B_1$, $B_2$, $B_6$ and $B_{12}$ and nicotinic acid and nicotinamide but also compounds with vitamin B properties such as adenine, choline, pantothenic acid, biotin, adenylic acid, folic acid, orotic acid, pangamic acid, carnitine, p-aminobenzoic acid, myo-inositol and lipoic acid, and vitamin C, vitamins of the D group, E group, F group, H group, I and J groups, K group and P group. Active ingredients for the purpose of the invention also include therapeutic peptides. Crop treatment agents include, for example, vinclozolin, epoxiconazole and quinmerac.

The process according to the invention is suitable, for example, for processing the following active ingredients:
acebutolol, acetylcysteine, acetylsalicylic acid, acyclovir, alprazolam, alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclomethasone, benserazide, benzalkoniumhydrochloride, benzocaine, benzoic acid, betamethasone, bezafibrate, biotin, biperiden, bisoprolol, bromazepam, bromhexine, bromocriptine, budesonide, bufexamac, buflomedil, buspirone, caffeine, camphor, captopril, carbamazepine, carbidopa, carboplatin, cefachlor, cefalexin, cefadroxil, cefazolin, cefixime, cefotaxime, ceftazidime, ceftriaxone, cefuroxime, selegiline, chloramphenicol, chlorhexidine, chlorpheniramine, chlortalidone, choline, cyclosporin, cilastatin, cimetidine, ciprofloxacin, cisapride, cisplatin, clarithromycin, clavulanic acid, clomipramine, clonazepam, clonidine, clotrimazole, codeine, cholestyramine, cromoglycic acid, cyanocobalamin, cyproterone, desogestrel, dexamethasone, dexpanthenol, dextromethorphan, dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidone, dopamine, doxycycline, enalapril, ephedrine, epinephrine, ergocalciferol, ergotamine, erythromycin, estradiol, ethinylestradiol, etoposide, Eucalyptus globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamicin, Ginkgo biloba, glibenclamide, glipizide, clozapine, Glycyrrhiza glabra, griseofulvin, guaifenesin, haloperidol, heparin, hyaluronic acid , hydrochlorothiazide, hydrocodone, hydrocortisone, hydromorphone, ipratropium hydroxide, ibuprofen, imipenem, indomethacin, iohexol, iopamidol, isosorbide dinitrate, isosorbide mononitrate, isotretinoin, ketotifen, ketoconazole, ketoprofen, ketorolac, labetalol, lactulose, lecithin, levocarnitine, levodopa, levoglutamide, levonorgestrel, levothyroxine, lidocaine, lipase, imipramine, lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin mixtures and combinations and mineral salts, N-methylephedrine, naftidrofuryl, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, pentoxifylline, phenoxymethylpenicillin, phenylephrine, phenylpropanolamine, phenytoin, piroxicam, polymyxin B, povidone-iodine, pravastatin, prazepam, prazosin, prednisolone, prednisone, bromocriptine, propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicylic acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamin E, folinic acid, zidovudine.

Preferred active ingredients are ibuprofen (as racemate, enantiomer or enriched enantiomer), ketoprofen, flurbiprofen, acetylsalicylic acid, verapamil, paracetamol, nifedipine or captopril.

Besides the obligatorily present agent which modifies the surface properties, the dosage forms obtained according to the invention may contain in the matrix conventional pharmaceutical ancillary substances, the total amount of which may be up to 100% by weight, based on the polymeric binder. Conventional pharmaceutical ancillary substances are, for example, extenders and bulking agents such as magnesium oxide, aluminum oxide, titanium oxide, stearic acid or salts thereof, e.g. the magnesium or calcium salt, methylcellulose, sodium carboxymethylcellulose, talc, sucrose, lactose, cereal or corn starch, potato flour, polyvinyl alcohol, in particular in a concentration of from 0.02 to 50, preferably 0.20 to 20, % by weight, based on the total weight of the mixture;

Lubricants such as aluminum and calcium stearates, talc and silicones, in a concentration of from 0.1 to 5, preferably 0.1 to 3, % by weight based on the total weight of the mixture;

Flow regulators such as animal or vegetable fats, in particular in hydrogenated form and those which are solid at room temperature. These fats preferably have a melting point of 50° C. or above. Triglycerides of $C_{12}$, $C_{14}$, $C_{16}$ and $C_{18}$ fatty acids are preferred. It is also possible to use waxes such as carnauba wax. These fats and waxes may be admixed advantageously alone or together with mono- and/or diglycerides or phosphatides, in particular lecithin. The mono- and diglycerides are preferably derived from the abovementioned fatty acid types. The total amount of fats, waxes, mono-, diglycerides and/or lecithins is 0.1 to 30, preferably 0.1 to 5, % by weight, based on the total weight of the composition for the particular layer;

Dyes such as azo dyes, organic or inorganic pigments or dyes of natural origin, with preference for inorganic pigments in a concentration of from 0.001 to 10, preferably 0.5 to 3, % by weight, based on the total weight of the mixture;

Stabilizers such as antioxidants, light stabilizers, hydroperoxide destroyers, radical scavengers, stabilizers against microbial attack.

It is also possible to add wetting agents, preservatives, disintegrants, adsorbents, mold release agents and blowing agents (cf., for example, H. Sucker et al., Pharmazeutische Technologie, Thieme-Verlag, Stuttgart 1978).

Ancillary substances for the purpose of the invention also means substances for producing a solid solution of the active ingredient. Examples of these ancillary substances are pentaerythritol and pentaerythritol tetraacetate, polymers such as polyethylene oxides and polypropylene oxides and their block copolymers (poloxamers), phosphatides such as lecithin, homo- and copolymers of vinylpyrrolidone, surfactants such as polyoxyethylene 40 stearate and citric and succinic acids, bile acids, sterols and others, as indicated, for example, by J. L. Ford, Pharm. Acta Helv. 61, 69–88 (1986).

Ancillary substances are also regarded as being bases and acids added to control the solubility of an active ingredient (see, for example, K. Thoma et al., Pharm. Ind. 51, 98–101 (1989)).

The only precondition for the suitability of ancillary substances is adequate thermal stability.

To produce the solid dosage forms, a plastic mixture of the components (melt) is prepared and is then subjected to a shaping step. The mixing of the components and the formation of the melt can take place in various ways. The mixing can take place before, during and/or after the formation of the melt. For example, the components can be first mixed and then melted or be mixed and melted simultaneously. The plastic mixture is often then homogenized in order to disperse the active ingredient thoroughly.

However, it has proven preferable, especially when sensitive active ingredients are used, first to melt the polymeric binder and, where appropriate, make a premix with conventional pharmaceutical additives, and then to mix in (homogenize) the sensitive active ingredient(s) in the plastic phase in intensive mixers with very short residence times. The active ingredient(s) can for this purpose be employed in solid form or in solution or dispersion.

The components are generally used as such in the production process. They can, however, also be used in liquid form, i.e in solution, suspension or dispersion.

Suitable solvents for the liquid form of the components are primarily water or a water-miscible organic solvent or a mixture thereof with water. However, it is also possible to use organic solvents which are immiscible or miscible with water. Suitable water-miscible solvents are, in particular, acetone, $C_1$–$C_4$-alkanols such as ethanol, isopropanol or n-propanol, polyols such as ethylene glycol, glycerol and polyethylene glycols. Suitable water-immiscible solvents are alkanes such as pentane or hexane, esters such as ethyl acetate or butyl acetate, chlorinated hydrocarbons such as methylene chlorie, and aromatic hydrocarbons such as toluene and xylene. Another solvent which can be used is liquid $CO_2$.

The solvent used in the individual case depends on the component to be taken up and the properties thereof. For example, active pharmaceutical ingredients are frequently used in the form of a salt which is, in general, soluble in water. Water-soluble active ingredients can therefore be employed as aqueous solution or, preferably, be taken up in the aqueous solution or dispersion of the binder. A corresponding statement applies to active ingredients which are soluble in one of the solvents mentioned, if the liquid form of the components used is based on an organic solvent.

It is possible where appropriate to replace melting by dissolving, suspending or dispersing in the abovementioned solvents, if desired and/or necessary with the addition of suitable ancillary substances such as emulsifiers. The solvent is then generally removed to form the melt in a suitable apparatus, e.g. an extruder. This will be comprised by the term mixing hereinafter.

The melting and/or mixing takes place in an apparatus customary for this purpose. Particularly suitable ones are extruders or containers which can be heated where appropriate and have an agitator, e.g. kneaders (like those of the type to be mentioned below).

A particularly suitable mixing apparatus is one employed for mixing in plastics technology. Suitable apparatuses are described, for example, in "Mischen beim Herstellen und Verarbeiten von Kunststoffen", H. Pahl, VDI-Verlag, 1986. Particularly suitable mixing apparatus are extruders and dynamic and static mixers, and stirred vessels, single-shaft stirrers with stripper mechanisms, especially paste mixers, multishaft stirrers, especially PDSM mixers, solids mixers and, preferably, mixer/kneader reactors (e.g. ORP, CRP, AP, DTB supplied by List or Reactotherm supplied by Krauss-Maffei or Ko-Kneader supplied by Buss), trough mixers and internal mixers or rotor/stator systems (e.g. Dispax supplied by IKA).

In the case of sensitive active ingredients it is preferable first for the polymeric binder to be melted in an extruder and then for the active ingredient to be admixed in a mixer/kneader reactor. On the other hand, with less sensitive active ingredients, a rotor/stator system can be employed for vigorously dispersing the active ingredient.

The mixing apparatus is charged continuously or batchwise, depending on its design, in a conventional way. Powdered components can be introduced in a free feed, e.g. via a weigh feeder. Plastic compositions can be fed in directly from an extruder or via a gear pump, which is particularly advantageous if the viscosities and pressures are high. Liquid media can be metered in via a suitable pump unit.

The mixture obtained by mixing and/or melting the binder, the active ingredient and, where appropriate, the additive or additives ranges from pasty to viscous (plastic) or fluid and is therefore extrudable. The glass transition temperature of the mixture is below the decomposition temperature of all the components present in the mixture. The binder should preferably be soluble or swellable in a physiological medium.

The steps of mixing and melting in the process can be carried out in the same apparatus or in two or more separately operating apparatuses. The preparation of a premix can take place in one of the conventional mixing apparatuses described above. A premix of this type can then be fed directly, for example into an extruder and subsequently extruded, where appropriate with the addition of other components.

It is possible in the process according to the invention to employ as extruders single screw machines, intermeshing screw machines or else multiscrew extruders, especially twin screw extruders, corotating or counterrotating and, where necessary, equipped with kneading disks. If it is necessary in the extrusion to evaporate a solvent, the extruders are generally equipped with an evaporating section. Particularly preferred extruders are those of the ZKS series from Werner & Pfleiderer.

The resulting mixture is preferably solvent-free, i.e. it contains neither water nor an organic solvent. The thermoformable extrudate of the plastic mixture is subjected to a definitive shaping to give the solid dosage forms using a mold. It is possible in this way to produce a large number of shapes depending on the mold and manner of shaping. For example, it is possible on use of an extruder to shape the extrudate between a belt and a roll, between two belts or between two rolls, as described in EP-A-358 105. It is particularly preferred to use a mold with two counterrotating molding rolls, of which at least one has depressions to receive and shape the plastic mixture. This type of shaping is normally referred to as calendering and is described, for example, in EP-A-240 904. Further shapes can be obtained by extrusion and hot or cold cut of the extrudate, for example small-particle and uniformly shaped granules. Hot-cut pelletization usually results in lenticular dosage forms (tablets) with a diameter of from 1 to 10 mm, whereas cold-cut pelletization normally results in cylindrical products with a length to diameter ratio of from 1 to 10 mm and a diameter of from 0.5 to 10 mm. It is possible in this way to produce, for example, oblong tablets, coated tablets, pastilles and pellets.

The application of the agent which modifies the surface properties to the surface of the plastic mixture can take place in a variety of ways. Thus, for example, the extruded plastic mixture can be passed through a bath or bed of the agent which modifies the surface properties. The agent which modifies the surface properties can be sprayed, painted, brushed or blown onto the preformed plastic mixture, for example using single-component or multicomponent nozzle systems. Transfer rolls can be used.

A particularly preferred process is one in which the agent which modifies the surface properties is initially applied in finely divided form to the surfaces of the mold which come into contact with the plastic mixture. Every contact of the surfaces of the mold with the plastic mixture is followed by a new application of the agent which modifies the surface properties. It is thus possible on use of a mold with two counterrotating molding rolls, at least one of which has depressions to receive and shape the plastic mixture (molding calender), for the molding rolls to be provided with the agent which modifies the surface properties. As soon as the plastic mixture enters the depressions, the soft, occasionally tacky surface of the plastic mixture takes up the agent which modifies the surface properties, and a permanent attachment between the two is brought about. Application of the agent which modifies the surface properties to the molding rolls can take place, for example, by the underside of the rolls passing through a bath, or by the agent being sprayed on or applied using brushes, e.g. using a circular brush with tubing connection.

Particularly good results have been obtained using the following agents which modify the surface properties, in the stated concentration (% by weight based on the dosage unit): magnesium stearate (0.01 to 0.3%), calcium stearate (0.01 to 0.3%), calcium behenate (0.01 to 0.3%), sodium stearylfumarate (0.01 to 1.0%), lecithin (e.g. egg/soybean) (0.01 to 0.5%), polyethylene glycol (0.01 to 1.0%), stearic acid, (0.01 to 1.0%), hydrogenated cottonseed oil (0.01 to 0.3%), hydrogenated castor oil (0.01 to 0.3%), talc (0.01 to 2.0%), rice starch (0.01 to 2.0%), calcium carbonate (0.01 to 1.0%), titanium dioxide (0.01 to 2.0%), highly disperse silica (0.01 to 0.1%), laked dyes (0.01 to 0.5%), iron oxide dyes (0.01 to 0.5%), silicones (0.01 to 0.5%), paraffins (0.01 to 0.5%), carnauba wax (0.01 to 0.5%), beeswax (0.01 to 0.5%), ethyl oleate (0.01 to 0.3%), stearyl alcohol (0.01 to 1.0%), surfactants, e.g. Cremophor EL (0.01 to 0.3%).

Liquid agents which modify the surface properties, such as polyethylene glycols, silicones, paraffins, ethyl oleate, can be applied directly by dipping the preformed plastic mixture or the mold surfaces or by brushing or spraying on. Substances which can be dissolved in a solvent, such as lecithin in water or alcohol, polyethylene glycol (with a molecular weight of more than 1000) in water, surfactants in water or, for example, alcohol, are applied as solution as described above. Substances which cannot be dissolved or can be dissolved only inadequately in a solvent, such as magnesium stearate, talc or waxes, are applied as suspension or dispersion in a solvent, where appropriate in combination with liquid or dissolved agents which modify the surface properties, as described above. Substances which cannot be dissolved or can be dissolved only inadequately and, in addition, are in very fine-particle form (particle sizes of less than about 50 μm), can be sprayed on through an air spraying device (two-component nozzles). These substances include, for example, magnesium stearate, calcium carbonate, sodium stearylfumarate, titanium dioxide and laked dyes. The spraying on can take place, depending on the required application rate, in the dry (without further ancillary substance) or suspended in a carrier such as water or polyethylene glycol, or in a rapidly evaporating solvent, e.g. acetone. The methods mentioned are preferably suitable for providing an agent which modifies the surface properties on an extruded product shortly before the calendering or on the mold surfaces which come into contact with the plastic mixture.

The process according to the invention has the following advantages: the solid dosage forms obtained according to the invention contain the agent which modifies the surface properties only on their surface, not throughout the composition. This makes it possible to reduce considerably the amount of agents which modify the surface properties. This in turn allows the dosage forms to be made considerably smaller for the same amount of active ingredient, which leads to a larger yield per batch and makes the production process more cost-effective. The agents which modify the surface properties used in the process according to the invention may also be those which are incompatible with one or more constituents of the tablet composition, because the agent which modifies the surface properties is substantially separated in space from the matrix of the dosage forms. It is possible to produce a stock batch of a pharmaceutical mixture which can be provided as required with different agents which modify the surface properties. Particularly on use of agents which modify the surface properties and have a lubricant action there is a reduction in the problems connected with the tackiness of the plastic mixture. The shaped dosage forms need not have completely cooled when leaving the mold, and the speed of manufacture can be increased without any disadvantage.

EXAMPLE

Extruded tablets of a vitamin B complex of the following composition were produced:

| | |
|---|---|
| Vitamin B complex | 13.32% |
| Klucel EF | 20.00% |
| Isomalt | 66.68% |

Lenticular tablets with a weight of 250.0 mg were produced.

For the production, the vitamin B complex, Klucel EF and isomalt were mixed in a container mixer for about 20 min and then extruded. The set parameters for the extrusion and the calender temperature in tests T 1 to T 3 are indicated below:

| Parameter | T 1 | T 2 | T 3 |
|---|---|---|---|
| Melt flow rate [kg/h] | 25 | 25 | 25 |
| Screw speed [rpm] | 130 | 130 | 130 |
| Vacuum [mbar] | 150 | 105 | 105 |
| Feed section temp. [° C.] | 23 | 23 | 23 |
| Section 1 temp. [° C.] | 80 | 80 | 80 |
| Section 2 temp. [° C.] | 100 | 100 | 100 |
| Section 3 temp. [° C.] | 110 | 110 | 110 |
| Section 4 temp. [° C.] | 110 | 110 | 110 |
| Head temp. [° C.] | 120 | 120 | 120 |
| Die temp. [° C.] | 120 | 120 | 125 |
| Calender temp. [° C.] | 18 | 12 | 30 |

It was not possible to detach the tablets from the molding rolls because of strong adhesion. In another test (T 4), the procedure of test T 3 was used but a dish filled with ethyl oleate was placed beneath each of the two calender rolls. The depth of immersion of the rolls in the liquid was such that all the indentations on the lowest point of the rolls were wetted (minimum immersion depth). The tablet composition described above could be removed from the molding rolls wetted in this way virtually without adhesion.

The increase in weight of the tablets due to the ethyl oleate, which was determined by weighing, was about 0.1% in this case.

In further tests, combinations of agents which modify the surface properties were employed, such as a suspension of 2% magnesium stearate in a mixture of 10% polyethylene glycol 600 in water. In this case, about 0.15% polyethylene glycol and about 0.03% magnesium stearate remained on the extruded tablets.

We claim:

1. A process for producing solid dosage forms by forming a plastic mixture of 10 to 99.9% by weight of at least one polymeric binder, 0.1 to 90% by weight of at least one active ingredient and, where appropriate, conventional additives, and shaping the solvent-free plastic mixture to the solid dosage forms using a mold, wherein an agent which modifies the surface properties is applied in finely divided form to the surface of the plastic mixture during the shaping, wherein the agent which modifies the surface properties is initially applied in finely divided form to the surfaces of the mold which come into contact with the plastic mixture to be shaped, and every contact of the surfaces of the mold with the plastic mixture is followed by a new application of the agent which modifies the surface properties.

2. A process as claimed in claim 1, wherein the mold comprises two counterrotating molding rolls of which at least one has depressions to receive and shape the plastic mixture.

3. A process as claimed in claim 2, wherein application of the agent which modifies the surface properties to the molding rolls takes place by the underside of the rolls passing through a bath, or by the agent being sprayed on or applied using brushes.

4. A process as claimed in claim 1, wherein the agent which modifies the surface properties is a surfactant.

5. A process as claimed in claim 1, wherein the agent which modifies the surface properties is a lipophilic compound which is selected from glycerides, waxes, fatty acids, fatty alcohols, paraffins, silicones and phosphatides.

6. A process as claimed in claim 1, wherein the agent which modifies the surface properties is an antioxidant.

7. A process as claimed in claim 1, wherein the agent which modifies the surface properties is a coloring agent.

8. A process as claimed in claim 1, wherein the agent which modifies the surface properties is an agent with antistatic effect and/or lubricant effect.

9. A process as claimed in claim 1, wherein the agent which modifies the surface properties comprises about 0.01 to about 1.0% by weight, based on the total weight of the resulting solid dosage form.

* * * * *